United States Patent
Chen et al.

(10) Patent No.: US 10,088,440 B2
(45) Date of Patent: Oct. 2, 2018

(54) HEAT DISSIPATION ESTIMATING METHOD

(71) Applicants: Inventec (Pudong) Technology Corporation, Shanghai (CN); INVENTEC CORPORATION, Taipei (TW)

(72) Inventors: Hua-Feng Chen, Taipei (TW); Wei-Yi Lin, Taipei (TW); Meng-Lung Chiang, Taipei (TW); Yu-Hsuan Lin, Taipei (TW)

(73) Assignees: Inventec (Pudong) Technology Corporation, Shanghai (CN); INVENTEC CORPORATION, Taipei (TW)

( * ) Notice: Subject to any disclaimer, the term of this patent is extended or adjusted under 35 U.S.C. 154(b) by 247 days.

(21) Appl. No.: 15/153,725

(22) Filed: May 12, 2016

(65) Prior Publication Data
US 2017/0153192 A1    Jun. 1, 2017

(30) Foreign Application Priority Data
Nov. 26, 2015   (CN) .......................... 2015 1 0837600

(51) Int. Cl.
| | | |
|---|---|---|
| *G01N 25/00* | (2006.01) | |
| *G01K 13/00* | (2006.01) | |
| *G01K 1/00* | (2006.01) | |
| *G01N 25/18* | (2006.01) | |
| *H05K 7/20* | (2006.01) | |
| *H01L 23/34* | (2006.01) | |

(52) U.S. Cl.
CPC ............. *G01N 25/18* (2013.01); *H01L 23/34* (2013.01); *H05K 7/2039* (2013.01)

(58) Field of Classification Search
USPC ............................................ 374/43, 29, 141
See application file for complete search history.

(56) References Cited

U.S. PATENT DOCUMENTS

| | | | | |
|---|---|---|---|---|
| 5,072,787 A | * | 12/1991 | Nakamichi | ........... H01L 23/467 165/146 |
| 6,422,307 B1 | * | 7/2002 | Bhatti | ...................... F28F 3/02 165/185 |
| 2012/0014063 A1 | * | 1/2012 | Weiss | ................ H05K 7/20163 361/697 |

* cited by examiner

*Primary Examiner* — Mirellys Jagan
(74) *Attorney, Agent, or Firm* — CKC & Partners Co., Ltd.

(57) ABSTRACT

A heat dissipation estimating method is disclosed. The heat dissipation estimating method includes following steps: providing an input heat to a fin of a heat sink unit; obtaining an average temperature of the fin according to the input heat; obtaining an output heat according to the average temperature; determining whether the input heat is the same as the output heat or not; while the input heat is different from the output heat, updating the input heat according to the output heat and repeating the above steps until the input heat is the same as the output heat; and while the input heat is the same as the output heat, obtaining a total heat dissipation value of the heat sink unit according to the input heat and a ratio value.

10 Claims, 4 Drawing Sheets

HEAT DISSIPATION ESTIMATING METHOD

RELATED APPLICATIONS

This application claims priority to Chinese Application Serial Number 201510837600.8, filed Nov. 26, 2015, which is herein incorporated by reference.

BACKGROUND

Technical Field

The present disclosure relates to a heat dissipation estimating method. More particularly, the present disclosure relates to the heat dissipation estimating method of a heat sink unit.

Description of Related Art

With the development of information technology, versatile electronic devices have been necessary to people, such as computers, mobile phones and panels. There are usually heat dissipation modules designed in the electronic devices because of highly dense logic circuits or memories thereof, and the heat dissipation modules can be classified into fan-type and non-fan type. The non-fan type heat dissipation modules would be necessary to be utilized under some specific circumstances, such as in factories, kitchens, hospitals and clean rooms. Because of the limited size of the electronic devices, it is important to estimate that hove large dissipation area is enough for dissipating, and evaluate how to optimize the design of the heat dissipation modules.

Generally, simulation software is utilized to construct three-dimensional structures of the dissipation modules and simulate the heat dissipation of the three-dimensional structures during the designing of the dissipation modules at the preset time. However, this kind of manner can only repeatedly modify the three-dimensional structures of the dissipation modules to estimate the total heat dissipated by the dissipation modules, and it will cost a lot of time and human resources.

SUMMARY

The following presents a simplified summary of the disclosure in order to provide a basic understanding to the reader. This summary is not an extensive overview of the disclosure and it does not identify key/critical components of the present disclosure or delineate the scope of the present disclosure. Its sole purpose is to present some concepts disclosed herein in a simplified form as a prelude to the more detailed description that is presented later.

In one aspect, the present disclosure is to provide a heat dissipation estimating method. The heat dissipation estimating method includes following steps: providing an input heat to a fin of a heat sink unit; obtaining an average temperature of the fin according to the input heat; obtaining an output heat according to the average temperature; determining whether the input heat is the same as the output heat or not; while the input heat is different from the output heat, updating the input heat according to the output heat and repeating the above steps until the input heat is the same as the output heat; and while the input heat is the same as the output heat, obtaining a total heat dissipation value of the heat sink unit according to the input heat and a ratio value.

In summary, the heat dissipation estimating method obtains the total heat dissipation value of the heat sink unit by determining whether the input heat and the output heat passing through the fin of the heat sink unit is equal. Therefore, not only the dissipation ability of the whole heat sink unit can be quickly estimated, but also the repeated modification can be prevented while utilizing the simulation software, and thus the waste of time and human resources can be reduced.

These and other features, aspects, and advantages of the present disclosure will become better understood with reference to the following description and appended claims.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1A:
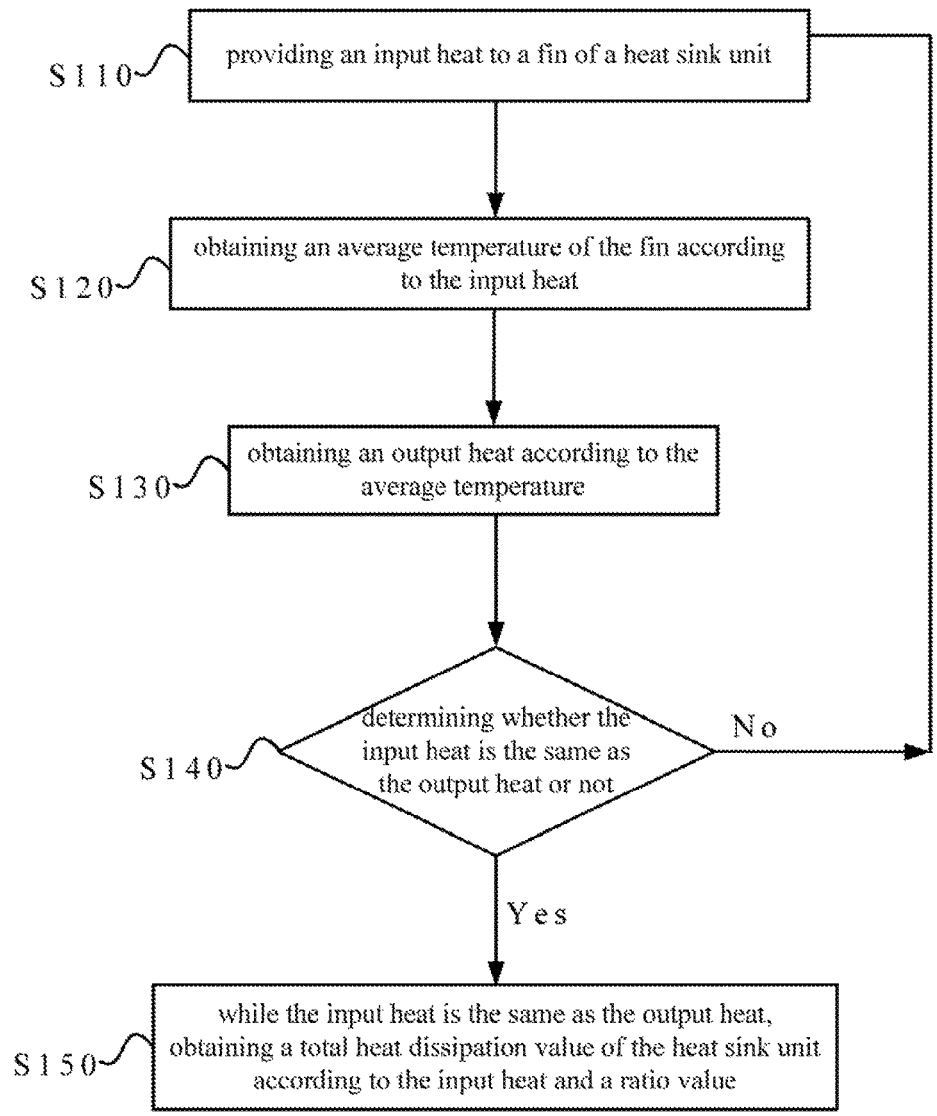
FIG. 1A is a schematic diagram of a heat dissipation estimating method in accordance with one embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description and claims, the terms "coupled" and "connected", along with their derivatives, may be used. In particular embodiments, "connected" and "coupled" may be used to indicate that two or more elements are in direct physical or electrical contact with each other, or may also mean that two or more elements may be in indirect contact with each other. "Coupled" and "connected" may still be used to indicate that two or more elements cooperate or interact with each other.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Figure 1B:
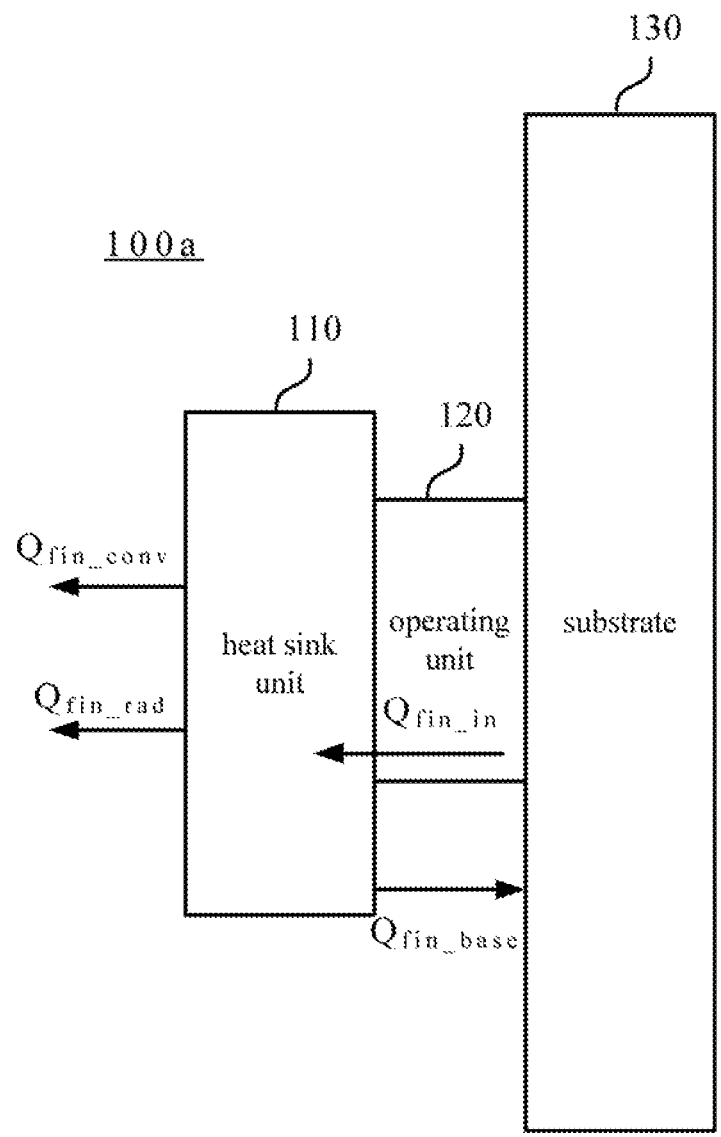
FIG. 1B is a schematic diagram of an electronic apparatus in accordance with one embodiment of the present disclosure.

Reference is made first to FIG. 1A and FIG. 1B. FIG. 1A is a schematic diagram of a heat dissipation estimating method 100 in accordance with one embodiment of the present disclosure. FIG. 1B is a schematic diagram of an electronic apparatus 100a in accordance with one embodiment of the present disclosure. As shown in FIG. 1B, the electronic apparatus 100a includes a heat sink unit 110, an operating unit 120 and a substrate 130. The electronic apparatus 100a can be a desktop computer, a notebook computer, a mobile phone, a panel or any electronic apparatus including heat sink units, and the present disclosure is not limited in this regard. It should be noted that the electronic apparatus 100a illustrated in the FIG. 1B can further include a storage unit, a battery or a casing in practical application, and it is just convenient for explaining such that only the heat sink unit 110, the operating unit 120 and the substrate 130 are illustrated in FIG. 1B.

The operating unit 120 can be a central processing unit (CPU), an arithmetic logic unit (ALU) or any logic circuit that has operating functions, and the present disclosure is not limited in this regard.

Figure 1C:
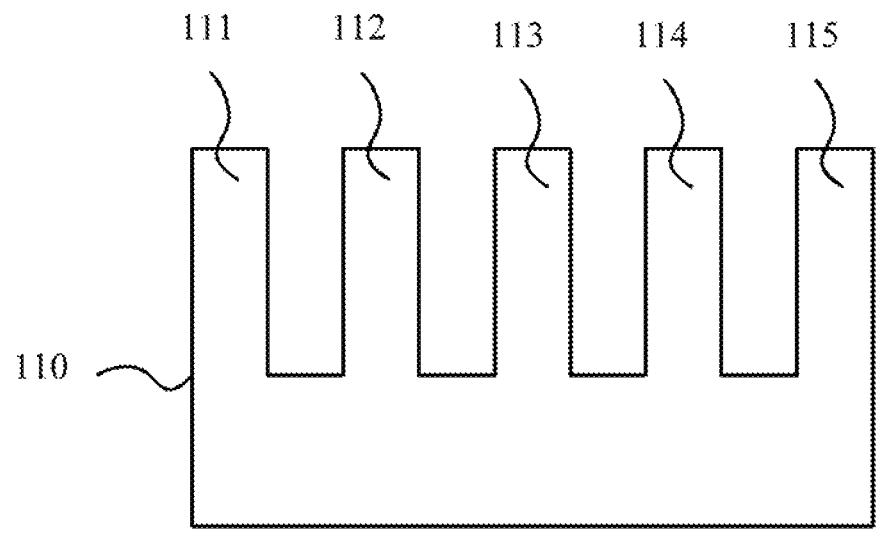
FIG. 1C is a schematic diagram of the heat sink unit in FIG. 1B.

As shown in FIG. 1B, the operating unit 120 is disposed on the substrate 130, which the substrate 130 can be a printed circuit board (PCB), a glass substrate or any substrate with different materials. The substrate 130 can include more than one operating unit 120, and the present disclosure is not limited in this regard. The reference is also made to FIG. 1C, and FIG. 1C is a schematic diagram of the heat sink unit 110 in FIG. 1B. In this embodiment, the heat sink unit 110 includes several fins 111~115, in practical application, the heat sink unit 110 can include only one fin or no fin, and the present disclosure is not limited in this regard.

The shape of the heat sink unit 110 can be square, rectangular, circular or any shape, and the material of the heat sink unit 110 can include iron, aluminum, copper or any material with good conductivity of heat. In addition, the heat sink unit 110 illustrated in FIG. 1B is just convenient for explaining the heat dissipation estimating method 100, and in practical application, the shape or the number of the fins 111~115 are not just limited to be the embodiment illustrated in FIG. 1B. The operating unit 120, such as CPU, would generate a lot of heat during operating, and the heat should be dissipated by the heat sink unit 110 to prevent the operating unit 120 from being overheated, and prevent the electronic apparatus 110a from malfunctioning or being shut down. Therefore, in this embodiment, the heat sink unit 110 is disposed just next to the operating unit 120 as shown in FIG. 1B, but the location of the heat sink unit 110 can be changed according to different needs of heat dissipation, and the present disclosure is not limited in this regard.

Reference is still made to FIG. 1A. The heat dissipation estimating method 100 executes Step S110 at first: providing an input heat $Q_{fin\_in}$ to the fin 111 of the heat sink unit 110. For further explanation, the whole volume of the heat sink unit 110 may be large, so the input heat $Q_{fin\_in}$ is only provided to one of the fins (e.g., the fin 111 in FIG. 1A) of the heat sink unit 110 during Step S110 of the heat dissipation estimating method 100 in this embodiment, and then a total heat dissipation value $Q_{tot}$ of the heat sink unit 110 can be obtained through a ratio value K during Step S150 of the heat dissipation estimating method 100, and it will be described in detail later. In other embodiments, Step S110 can provide the input heat $Q_{fin\_in}$ to one of the other fins (fins 112~115), or to several fins of the heat sink unit 110 at the same time. For example, Step S110 can provide the input heat $Q_{fin\_in}$ to the fins 112, 113 at the same time, or provide the input heat $Q_{fin\_in}$ to the fins 112, 114, 115 at the same time, or provide the input heat $Q_{fin\_in}$ to the fins 111~115 at the same time, and the present disclosure is not limited in this regard.

Figure 2:
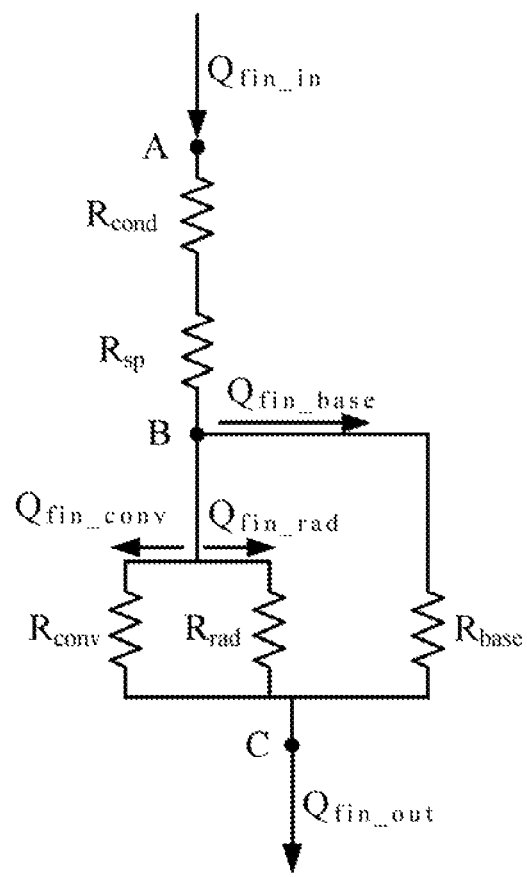
FIG. 2 is a schematic diagram of a heat equivalent circuit of the heat sink unit in FIG. 1B.

The heat dissipation estimating method 100 then executes Step S120: obtaining an average temperature $T_{fin\_avg}$ of the fin 111 according to the input heat $Q_{fin\_in}$. For further explanation, Step S120 obtains the average temperature $T_{fin\_avg}$ according to the input heat $Q_{fin\_in}$, a conducting thermal resistance $R_{cond}$ of the fin, a spreading thermal resistance $R_{sp}$ of the fin 111 and a highest temperature $T_{max}$ of the fin. The reference is also made to FIG. 2. FIG. 2 is a schematic diagram of a heat equivalent circuit 200 of the heat sink unit 110 in FIG. 1B. The heat equivalent circuit 200 includes a conducting thermal resistor $R_{cond}$, a spreading thermal resistor $R_{sp}$, a convecting thermal resistor $R_{conv}$, a radiating thermal resistor $R_{rad}$ and a substrate thermal resistor $R_{base}$. It should be noted that, the heat equivalent circuit 200 does not follow the ohm's law as usual circuits, but follows the theorems of thermodynamics, and the relations of the ohm's law and the theorems of thermodynamics can be shown as formula (1) and formula (2) respectively as below:

$$V = I \times R \quad \text{formula (1); and}$$

$$T = Q \times R \quad \text{formula (2).}$$

V is voltage, I is current and R is resistance in the formula (1). T is temperature, Q is heat and R is thermal resistance in the formula (2). Therefore, the relation of the heat and the temperature between a node A and a node B of the heat equivalent circuit 200 can be shown as formula (3) as below:

$$T_{fin\_avg} = T_{max} - (R_{cond} + R_{sp}) \times Q_{fin\_in} \quad \text{formula (3).}$$

$T_{fin\_avg}$ is the average temperature, i.e., the temperature of the node B, $T_{max}$ is the largest temperature, i.e., the temperature of the node A, $R_{cond}$ is the conducting thermal resistance, $R_{sp}$ is the spreading thermal resistance and $Q_{fin\_in}$ is the input heat. The conducting thermal resistance $R_{cond}$ and the spreading thermal resistance $R_{sp}$ are influenced according to different materials of the heat sink unit 110 and the operating unit 120. Actually, the abovementioned formula (3) is the formula of Step S120: obtaining the average temperature $T_{fin\_avg}$ according to the input heat $Q_{fin\_in}$, the conducting thermal resistance $R_{cond}$ of the fin, the spreading thermal resistance $R_{sp}$ of the fin 111 and the highest temperature $T_{max}$ of the fin.

The heat dissipation estimating method 100 then executes Step S130: obtaining an output heat $Q_{fin\_out}$ according to the average temperature $T_{fin\_avg}$. For further explanation, Step S130 obtains the output heat $Q_{fin\_out}$ according to a dissipated heat by convection $Q_{fin\_conv}$ of the fin 111, a dissipated heat by radiation $Q_{fin\_rad}$ of the fin 111 and a substrate dissipation heat $Q_{fin\_base}$ of the fin 111. Therefore, as shown in FIG. 2, the relation of the heat between the node B and a node C can be shown as formula (4) as below:

$$Q_{fin\_out} = Q_{fin\_conv} + Q_{fin\_rad} + Q_{fin\_base} \quad \text{formula (4).}$$

$Q_{fin\_out}$ is the output heat, $Q_{fin\_conv}$ is the dissipated heat by convection, $Q_{fin\_rad}$ is the dissipated heat by radiation and $Q_{fin\_base}$ is the substrate dissipation heat. Actually, the abovementioned formula (4) is the formula of Step S130: obtaining the output heat $Q_{fin\_out}$ according to the dissipated heat by convection $Q_{fin\_conv}$ of the fin 111, the dissipated heat by radiation $Q_{fin\_rad}$ of the fin 111 and the substrate dissipation heat $Q_{fin\_base}$ of the fin 111. As shown in FIG. 1B, the heat sink unit 110 can exhaust the received input heat $Q_{fin\_in}$ through convecting (the dissipated heat by convection $Q_{fin\_conv}$), radiating (the dissipated heat by radiation $Q_{fin\_rad}$) or flowing to the substrate (the substrate dissipation heat $Q_{fin\_base}$).

In addition, the abovementioned dissipated heat by convection $Q_{fin\_conv}$ can be obtained according to a surface area A of the fin 111, the average temperature $T_{fin\_avg}$ and an ambient temperature Ta. Therefore, as shown in FIG. 2, the relation of the heat flowing through the convecting thermal resistor $R_{conv}$ can be shown as formula (5) as below:

$$Q_{fin\_conv} = h \times A \times (T_{fin\_avg} - T_a) \qquad \text{formula (5)}.$$

$Q_{fin\_conv}$ is the dissipated heat by convection, h is a convection heat-dissipation coefficient, A is the surface area of the fin 111, $T_{fin\_avg}$ is the average temperature, i.e., the temperature of the node B, and $T_a$ is the ambient temperature, i.e., the temperature of the node C. Actually, the abovementioned formula (5) is the formula of obtaining the dissipated heat by convection $Q_{fin\_conv}$ according to the surface area A of the fin 111 the average temperature $T_{fin\_avg}$ and the ambient temperature Ta. On the other hand, the abovementioned dissipated heat by radiation $Q_{fin\_rad}$ can be obtained according to the surface area A of the fin 111, the average temperature $T_{fin\_avg}$ and the ambient temperature Ta. Therefore, as shown in FIG. 2, the relation of the heat flowing through the radiating thermal resistor $R_{rad}$ can be shown as formula (6) as below:

$$Q_{fin\_rad} = \varepsilon \times A \times (T_{fin\_avg} - T_a) \qquad \text{formula (6)}.$$

$Q_{fin\_rad}$ is the dissipated heat by radiation, ε is a radiation heat-dissipation coefficient, A is the surface area of the fin, $T_{fin\_avg}$ is the average temperature and $T_a$ is the ambient temperature. Actually, the abovementioned formula (6) is the formula of obtaining the dissipated heat by radiation $Q_{fin\_rad}$ according to the surface area A of the fin 111, the average temperature $T_{fin\_avg}$ and the ambient temperature Ta. It should be noted that, the dissipated heat by convection $Q_{fin\_conv}$ and the dissipated heat by radiation $Q_{fin\_rad}$ is proportional to the surface area A of the fin 111, that is to say, if the surface area A of the fin 111 is bigger, the the dissipated heat by convection $Q_{fin\_conv}$ and the dissipated heat by radiation $Q_{fin\_rad}$ will be larger too.

The heat dissipation estimating method 100 then executes Step S140: determining whether the input heat $Q_{fin\_in}$ is the same as the output heat $Q_{fin\_out}$ or not; while the input heat $Q_{fin\_in}$ is different from the output heat $Q_{fin\_out}$, updating the input heat $Q_{fin\_in}$ according to the output heat $Q_{fin\_out}$ and repeating the above steps S110~S130 until the input heat $Q_{fin\_in}$ is the same as the output heat $Q_{fin\_out}$. For further explanation, the abovementioned Step 140 updates the input heat $Q_{fin\_in}$ according to the output heat $Q_{fin\_out}$ can be such as while the input heat $Q_{fin\_in}$ is lower than the output heat $Q_{fin\_out}$, and it does not follow the energy conservation law, so Step 140 increases the input heat $Q_{fin\_in}$ and repeats the above steps S110~S130 until the input heat $Q_{fin\_in}$ is the same as the output heat $Q_{fin\_out}$. Similarly, while the input heat $Q_{fin\_in}$ is higher than the output heat $Q_{fin\_out}$, and it does not follow the energy conservation law, so Step 140 decreases the input heat $Q_{fin\_in}$ and repeats the above steps S110~S130 until the input heat $Q_{fin\_in}$ is the same as the output heat $Q_{fin\_out}$.

The heat dissipation estimating method 100 then executes Step S150: while the input heat $Q_{fin\_in}$ is the same as the output heat $Q_{fin\_out}$, obtaining a total heat dissipation value $Q_{tot}$ of the heat sink unit 110 according to the input heat $Q_{fin\_in}$ and a ratio value K. For further explanation, in this embodiment, the ration value K can be a ratio of the fin 111 to the whole heat sink unit 110, such as 0.2 (one fifth). Or in some embodiments, Step S110 provides the input heat $Q_{fin\_in}$ to the fins 112, 114, 115 at the same time, the ratio value K can be a ratio of the fins 112, 114, 115 to the whole heat sink unit 110, such as 0.6 (three fifths). However, in practical application, the ratio value K can be any number, and the present disclosure is not limited in this regard. Thus, the heat dissipation estimating method obtains the total heat dissipation value of the heat sink unit by determining whether the input heat and the output heat passing through the fin of the heat sink unit is equal. Therefore, not only the dissipation ability of the whole heat sink unit can be quickly estimated, but also the repeated modification can be prevented while utilizing the simulation software, and thus the waste of time and human resources can be reduced.

The present disclosure relates to a heat dissipation estimating method. More particularly, the present disclosure relates to the heat dissipation estimating method of a heat sink unit. The heat dissipation estimating method obtains the total heat dissipation value of the heat sink unit by determining whether the input heat and the output heat passing through the fin of the heat sink unit is equal. Therefore, not only the dissipation ability of the whole heat sink unit can be quickly estimated, but also the repeated modification can be prevented while utilizing the simulation software, and thus the waste of time and human resources can be reduced.

The above illustrations include exemplary operations, but the operations are not necessarily performed in the order shown. Operations may be added, replaced, changed order, and/or eliminated as appropriate, in accordance with the spirit and scope of various embodiments of the present disclosure.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A heat dissipation estimating method, comprising:
   providing an input heat to a fin of a heat sink unit;
   obtaining an average temperature of the fin according to the input heat;
   obtaining an output heat according to the average temperature;
   determining whether the input heat is the same as the output heat or not;
   when the input heat is different from the output heat, updating the input heat according to the output heat and repeating the above steps until the input heat is the same as the output heat; and when the input heat is the same as the output heat, obtaining a total heat dissipation value of the heat sink unit according to the input heat and a ratio value.

2. The heat dissipation estimating method of claim 1, further comprising:
when the input heat is lower than the output heat, increasing the input heat; and
when the input heat is higher than the output heat, decreasing the input heat.

3. The heat dissipation estimating method of claim 1, further comprising:
obtaining the average temperature according to the input heat, a conducting thermal resistance of the fin, a spreading thermal resistance of the fin and a highest temperature of the fin.

4. The heat dissipation estimating method of claim 3, wherein a formula for obtaining the average temperature according to the input heat, the conducting thermal resistance of the fin, the spreading thermal resistance of the fin and the highest temperature of the fin is:

$$T_{fin\_avg} = T_{max} - (R_{cond} + R_{sp}) \times Q_{fin\_in},$$

and $T_{fin\_avg}$ is the average temperature, $T_{max}$ is the highest temperature, $R_{cond}$ is the conducting thermal resistance, $R_{sp}$ is the spreading thermal resistance and $Q_{fin\_in}$ is the input heat.

5. The heat dissipation estimating method of claim 1, further comprising:
obtaining the output heat according to a dissipated heat by convection of the fin, a dissipated heat by radiation of the fin and a substrate dissipation heat of the fin.

6. The heat dissipation estimating method of claim 5, wherein a formula for obtaining the output heat according to the dissipated heat by convection of the fin, the dissipated heat by radiation of the fin and the substrate dissipation heat of the fin is:

$$Q_{fin\_out} = Q_{fin\_conv} + Q_{fin\_rad} + Q_{fin\_base},$$

and $Q_{fin\_out}$ is the output heat, $Q_{fin\_conv}$ is the dissipated heat by convection, $Q_{fin\_rad}$ is the dissipated heat by radiation and $Q_{fin\_base}$ is the substrate dissipation heat.

7. The heat dissipation estimating method of claim 5, further comprising:
obtaining the dissipated heat by convection of the fin according to a surface area of the fin, the average temperature and an ambient temperature.

8. The heat dissipation estimating method of claim 7, wherein a formula for obtaining the dissipated heat by convection of the fin according to the surface area of the fin, the average temperature and the ambient temperature is $$Q_{fin\_conv} = h \times A \times (T_{fin\_avg} - T_a),$$

and $Q_{fin\_conv}$ is the dissipated heat by convection, h is a convection heat-dissipation coefficient, A is the surface area of the fin, $T_{fin\_avg}$ is the average temperature and $T_a$ is the ambient temperature.

9. The heat dissipation estimating method of claim 5, further comprising:
obtaining the dissipated heat by radiation of the fin according to a surface area of the fin, the average temperature and an ambient temperature.

10. The heat dissipation estimating method of claim 9, wherein a formula for obtaining the dissipated heat by radiation of the fin according to the surface area of the fin, the average temperature and the ambient temperature is:

$$Q_{fin\_rad} = \varepsilon \times A \times (T_{fin\_avg} - T_a),$$

and $Q_{fin\_rad}$ is the dissipated heat by radiation, $\varepsilon$ is a radiation heat-dissipation coefficient, A is the surface area of the fin, $T_{fin\_avg}$ is the average temperature and $T_a$ is the ambient temperature.

* * * * *